(12) United States Patent
Imamura et al.

(10) Patent No.: US 8,980,586 B2
(45) Date of Patent: Mar. 17, 2015

(54) COMPOUND AND METHOD FOR PRODUCING SAME

(71) Applicants: The Ritsumeikan Trust, Kyoto (JP); National University Corporation Shizuoka University, Shizuoka (JP)

(72) Inventors: Nobutaka Imamura, Shiga (JP); Kazuya Nakagawa, Shiga (JP); Shinji Tokuyama, Shizuoka (JP)

(73) Assignees: The Ritsumeikan Trust, Kyoto (JP); National University Corporation Shizuoka University, Shizuoka (JP)

( * ) Notice: Subject to any disclaimer, the term of this patent is extended or adjusted under 35 U.S.C. 154(b) by 0 days.

(21) Appl. No.: 14/353,888

(22) PCT Filed: Oct. 22, 2012

(86) PCT No.: PCT/JP2012/077229
§ 371 (c)(1),
(2) Date: Apr. 24, 2014

(87) PCT Pub. No.: WO2013/061919
PCT Pub. Date: May 2, 2013

(65) Prior Publication Data
US 2014/0309438 A1  Oct. 16, 2014

(30) Foreign Application Priority Data
Oct. 25, 2011  (JP) .................. 2011-233692

(51) Int. Cl.
C07D 309/32 (2006.01)
C07D 493/14 (2006.01)
(Continued)

(52) U.S. Cl.
CPC .............. C07D 309/30 (2013.01); C12R 1/465 (2013.01); A01N 43/16 (2013.01); A61K 31/351 (2013.01); C07D 309/32 (2013.01); C12P 1/06 (2013.01); C12P 15/00 (2013.01); C12P 17/06 (2013.01); C12P 17/181 (2013.01); A01N 43/90 (2013.01); C07D 493/14 (2013.01); C12P 17/162 (2013.01)
USPC ............ 435/118; 435/119; 549/359; 549/415

(58) Field of Classification Search
None
See application file for complete search history.

(56) References Cited

U.S. PATENT DOCUMENTS 5,420,261 A  5/1995 Chu et al.

FOREIGN PATENT DOCUMENTS

EP  0 191 399  8/1986
JP  61-183278  8/1986
(Continued)

OTHER PUBLICATIONS

Nakagawa et al., Journal of Antibiotics (2012), 65(12), 599-607.*
(Continued)

*Primary Examiner* — Sun Jae Yoo
(74) *Attorney, Agent, or Firm* — Wenderoth, Lind & Ponack, L.L.P.

(57) ABSTRACT

An object of the present invention is to provide a novel compound useful as an antifungal substance and a method for producing the compound. The present invention relates to a compound represented by Formula ($I_0$) or a salt thereof, and a method for producing the compound using a microorganism:

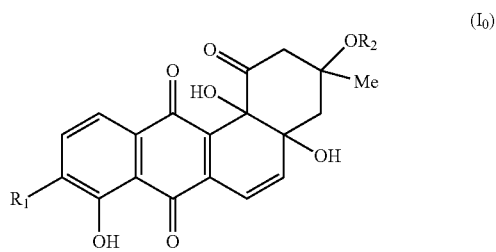

wherein $R_1$ is:

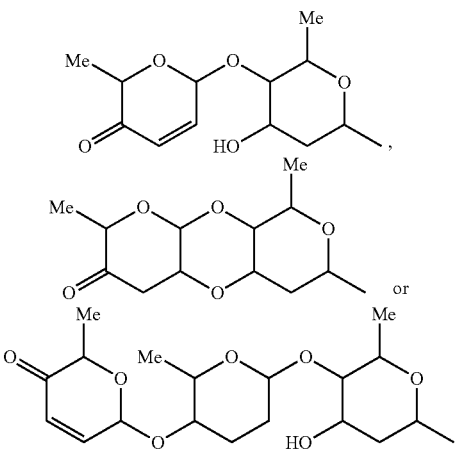

and $R_2$ is:

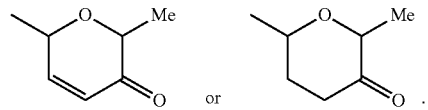

6 Claims, No Drawings

(51) Int. Cl.

| | |
|---|---|
| *C07D 309/30* | (2006.01) |
| *A01N 43/90* | (2006.01) |
| *A01N 43/16* | (2006.01) |
| *A01N 63/02* | (2006.01) |
| *A61K 31/351* | (2006.01) |
| *C12R 1/465* | (2006.01) |
| *C12P 1/06* | (2006.01) |
| *C12P 15/00* | (2006.01) |
| *C12P 17/06* | (2006.01) |
| *C12P 17/18* | (2006.01) |
| *C12P 17/16* | (2006.01) |

(56) References Cited

FOREIGN PATENT DOCUMENTS

| JP | 4-178379 | 6/1992 |
|---|---|---|
| JP | 5-236843 | 9/1993 |
| JP | 11-266733 | 10/1999 |
| JP | 2007-254463 | 10/2007 |
| KR | 10-2006-0016155 | 2/2006 |
| WO | 2006/101060 | 9/2006 |

OTHER PUBLICATIONS

International Search Report issued Dec. 18, 2012 in International (PCT) Application No. PCT/JP2012/077229.

Chu et al., "Sch 47554 and Sch 47555, Two Novel Antifungal Antibiotics Produced from a *Streptomyces* sp.", The Journal of Antibiotics, vol. 46, No. 5, 1993, pp. 861-865.

Uchida et al., "Saquayamycins, New Aquayamycin-Group Antibiotics", The Journal of Antibiotics, vol. 38, No. 9, 1985, pp. 1171-1181.

Chihara, M., "3-3 Phylogeny of Eukaryotic Algae", Diversity and Evolution of Algae, 1999, pp. 39-43, with English translation and cited in specification.

Egusa, S., "2. Water mold disease", Infectious and Parasitic Diseases of Fish and Shellfish, 2004, pp. 265-268, with English translation and cited in specification.

Material Safety Data Sheet (MSDS) "Safety data for 2-bromo-2-nitro-1,3-propanediol", Product Code: #0585, 2007.

\* cited by examiner

```
                         SEQUENCE LISTING

<160> NUMBER OF SEQ ID NOS: 1

<210> SEQ ID NO 1
<211> LENGTH: 1516
<212> TYPE: DNA
<213> ORGANISM: Streptomyces sp.TK08046

<400> SEQUENCE: 1
gagtttgatc ctggctcagg acgaacgctg gcggcgtgct taacacatgc aagtcgaacg      60
atgaagccct tcggggtgga ttagtggcga acgggtgagt aacacgtggg caatctgccc     120
ttcactctgg gacaagccct ggaaacgggg tctaataccg gataccactc tcgcgggcat     180
ctgtgagggt tgaaagctcc ggcggtgaag gatgagcccg cggcctatca gcttgttggt     240
gaggtaacgg ctcaccaagg cgacgacggg tagccggcct gagagggcga ccggccacac     300
tgggactgag acacggccca gactcctacg ggaggcagca gtggggaata ttgcacaatg     360
ggcgaaagcc tgatgcagcg acgccgcgtg agggatgacg gccttcgggt tgtaaacctc     420
tttcagcagg gaagaagcga aagtgacggt acctgcagaa gaagcgccgg ctaactacgt     480
gccagcagcc gcggtaatac gtagggcgca agcgttgtcc ggaattattg gtcgtaaaga     540
gctcgtaggc ggcttgtcac gtcgggtgtg aaagcccggg gcttaacccc gggtctgcat     600
tcgatacggg ctagctagag tgtggtaggg gagatcggaa ttcctggtgt agcggtgaaa     660
tgcgcagata tcaggaggaa caccggtggc gaaggcggat ctctgggcca ttactgacgc     720
tgaggagcga aagcgtgggg agcgaacagg attagatacc ctggtagtcc acgccgtaaa     780
cggtgggaac taggtgttgg cgacattcca cgtcgtcggt gccgcagcta acgcattaag     840
ttccccgcct ggggagtacg gccgcaaggc taaaactcaa aggaattgac gggggcccgc     900
acaagcagcg gagcatgtgg cttaattcga cgcaacgcga agaaccttac caaggcttga    960
catacaccgg aaaaccctgg agacagggtc ccccttgtgg tcggtgtaca ggtggtgcat    1020
ggctgtcgtc agctcgtgtc gtgagatgtt gggttaagtc ccgcaacgag cgcaacccttt   1080 gttctgtgtt gccagcatgc ccttcggggt gatgggact cacaggagac cgccggggtc    1140
aactcggagg aaggtgggga cgacgtcaag tcatcatgcc ccttatgtct tgggctgcac    1200
acgtgctaca atggccggta caaagagctg cgataccgtg aggtggagcg aatctcaaaa    1260
agccggtctc agttcggatt ggggtctgca actcgacccc atgaagtcgg agttgctagt    1320
aatcgcagat cagcattgct gcggtgaata cgttcccggg ccttgtacac accgcccgtc    1380
```

```
acgtcacgaa agtcggtaac acccgaagcc ggtggcccaa ccccttgtgg gagggagctg    1440
tcgaaggtgg gactggcgat tgggacgaag tcgtaacaag gtagccgtac cggatgtgcg    1500
gctggatcac ctcctt                                                   1516
```

COMPOUND AND METHOD FOR PRODUCING SAME

TECHNICAL FIELD

The present invention relates to a novel compound usable as an antifungal substance, and a method for producing the compound using a microorganism.

BACKGROUND ART

A fish disease called saprolegniasis has long been a problem in farms of freshwater fish such as rainbow trout. Saprolegniasis is caused by species belonging to genera *Saprolegnia*, *Achlya*, and *Aphanomyces* of family Saprolegniaceae, order Saprolegniales, class Oomycetes. Recent molecular analysis and biochemical research has confirmed that oomycetes are classified as Heterokontae in the kingdom Protista, that oomycetes have a fungus-like appearance (Non-patent Literature (NPL) 1), and that the genus *Phytophthora*, which is plant-pathogenic, also belongs to this group.

Malachite green dye, which is active even at low concentrations against saprolegniasis-causing organisms (NPL 2) and is inexpensive, has been used as a prophylactic and therapeutic agent. In recent years, however, due to concerns about its carcinogenicity, malachite green has been banned for use with farmed edible fish. As a substitute saprolegniasis prophylactic medication for farmed fish or fish eggs, ozone (Patent Literature (PTL) 1), electrolyzed water (PTL 2), organic acids (PTL 3), *Bacillus subtilis* strains (PTL 4), etc., have been proposed. Further, medications such as Pyceze (trade name, a product of Novartis Animal Health K.K.), which comprises the synthetic antimicrobial preservative bronopol ($C_3H_6BrNO_4$) as an active ingredient, are commercially available. However, Pyceze is expensive compared to malachite green, and the active ingredient bronopol has observable potent toxicity in aquatic organisms such as edible oysters ($EC_{50}$ 0.77 mg/L), water fleas ($EC_{50}$ 1.4 mg/L), which are useful as fish feed, and green algae ($EC_{50}$ 0.0537 mg/L) (NPL 3). Therefore, Pyceze has problems such as requiring dilution with a large amount of water upon disposal. Accordingly, there is a need for the development of a safer and effective antifungal agent.

CITATION LIST

Patent Literature

PTL 1: JPH05-236843A
PTL 2: JPH11-266733A
PTL 3: JP2007-254463A
PTL 4: WO2006/101060

Non-Patent Literature

NPL 1: Mitsuo Chihara, Diversity and Evolution of Algae, Shokabo Publishing Co., Ltd. (1999)
NPL 2: Shuzo Egusa, Infectious and Parasitic Diseases of Fish and Shellfish, Koseisha-Koseikaku Corporation (2004)
NPL 3: Material Safety Data Sheet Product Code: #0585 (2007)

SUMMARY OF INVENTION

Technical Problem

In view of the above circumstances, the present invention aims to search for a novel antifungal substance from natural source to provide the novel substance and a production method thereof.

Solution to Problem

The present inventors conducted extensive research to solve the above problem and found that a compound obtained from a culture medium of a microorganism belonging to the genus *Streptomyces* is a selective antifungal substance. The present invention has been accomplished based on this finding. The present invention encompasses the following inventions:

(1) A compound represented by Formula ($I_0$) or a salt thereof:

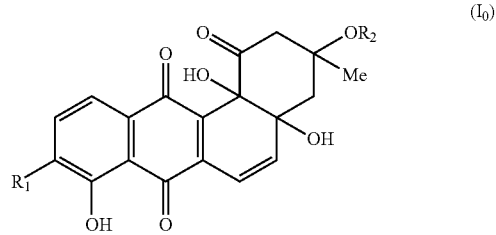

wherein $R_1$ is:

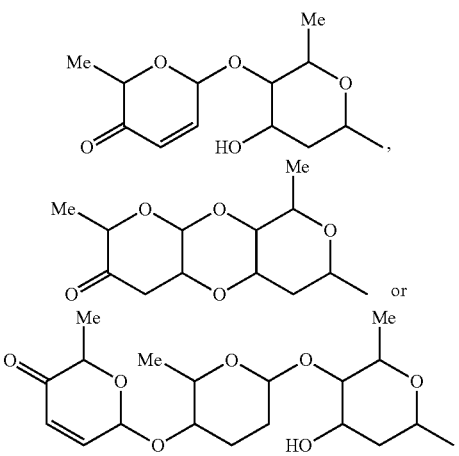

and $R_2$ is:

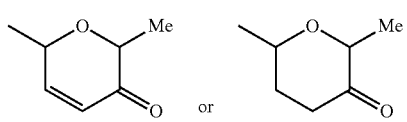

(2) A compound represented by Formula (I) or a salt thereof:

(I)

[Chemical structure of Formula (I) showing a tetracyclic compound with Me, RO, HO, OH, O, OH, HO, Me, O, Me substituents]

wherein R is:

[Two chemical structures showing R groups: first with O, Me, Me substituents; second with Me, Me, O, O substituents] or (3) A method for producing the compound of (1) or (2), wherein the method comprises culturing a microorganism belonging to the genus *Streptomyces* having the ability to produce the compound of (1) or (2) in a medium to produce and accumulate the compound in a culture product; and collecting the compound.

(4) An antifungal agent comprising the compound of (1) or (2) as an active ingredient.

Advantageous Effects of Invention

The present invention provides a novel antifungal substance, and a method for producing the substance using a microorganism. The compound of the present invention exhibits extremely high antifungal activity, and has a very low effect on the ecosystem. Accordingly, the compound of the present invention is effective as antifungal agent, more specifically, as an agent for preventing or treating fish diseases, or as an agent for controlling plant diseases caused by oomycetes.

DESCRIPTION OF EMBODIMENTS

The present invention is explained in detail below.

The compound of the present invention is a compound isolated and purified from streptomycetes (*Streptomyces* sp. TK08046, etc.), and has an antifungal activity. The properties of the compound of the present invention and the production method thereof are explained in detail below.

1. The Properties of the Compound of the Present Invention:

The compound of the present invention is represented by Formula ($I_0$) or a salt thereof:

($I_0$)

[Chemical structure of Formula ($I_0$) showing a tetracyclic compound with O, OR$_2$, HO, Me, OH, $R_1$, OH, O substituents]

wherein $R_1$ is:

[Three chemical structures for $R_1$ group]

and $R_2$ is:

[Two chemical structures for $R_2$ group with Me, O substituents] or

Hereunder, this compound may be referred to as "Compound of Formula ($I_0$)."

Compound of Formula ($I_0$) includes at least one member selected from the group consisting of the compounds described below:

A compound represented by Formula ($I_0$):

($I_0$)

[Chemical structure of Formula ($I_0$) showing the tetracyclic compound with O, OR$_2$, HO, Me, OH, $R_1$, OH, O substituents]

wherein $R_1$ is:

and $R_2$ is:

Hereunder, this compound may be referred to as Compound $(I_0\text{-A})$;

in Formula $(I_0)$, $R_1$ is:

and $R_2$ is:

Hereunder, this compound may be referred to as "Compound $(I_0\text{-B})$";

in Formula $(I_0)$, $R_1$ is:

and $R_2$ is:

Hereunder, this compound may be referred to as "Compound $(I_0\text{-C})$";

in Formula $(I_0)$, $R_1$ is:

and $R_2$ is:

Hereunder, this compound may be referred to as "Compound $(I_0\text{-D})$"; and in Formula $(I_0)$, $R_1$ is:

and $R_2$ is:

Hereunder, this compound may be referred to as "Compound $(I_0\text{-E})$."

Among the above compounds represented by Formula $(I_0)$, the compound represented by Formula (I) below is preferable:

(I)

wherein R is:

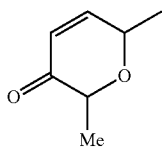

or

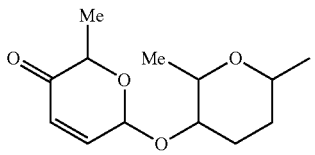 [SMILES: CC1CCC(OC2C=CC(=O)C(C)O2)C(C)O1]

Hereunder, this compound may be referred to as "Compound of Formula (I)."

Compound of Formula (I) includes:

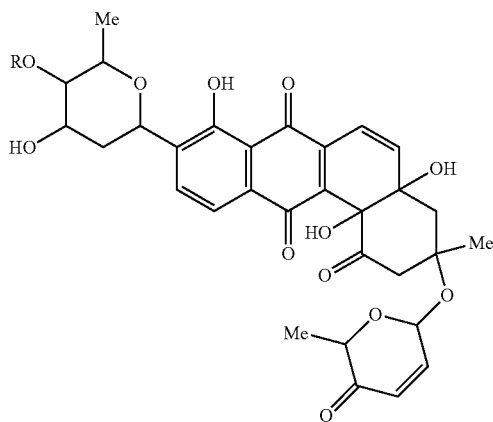

(I)

in Formula (I), R is:

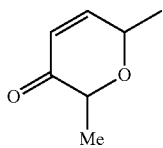

Hereunder, this compound may be referred to as "Compound (I-1)," and/or R is:

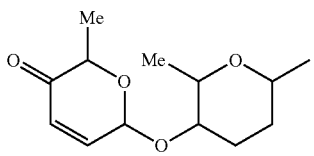 [SMILES: CC1CCC(OC2C=CC(=O)C(C)O2)C(C)O1]

Hereunder, this compound may be referred to as "Compound (I-2)." Compound (I-1) corresponds to the above-mentioned Compound ($I_0$-A), and Compound (I-2) corresponds to the above-mentioned Compound ($I_0$-E).

Compounds ($I_0$-A) to ($I_0$-E) can form a salt (in particular, a base addition salt) in accordance with a conventional procedure. The salts of the compound thus formed are included in the scope of the present invention.

Examples of the base addition salts of Compounds ($I_0$-A) to ($I_0$-E) include salts with an inorganic base or an organic base. Examples of salts with inorganic bases include ammonium salts, alkali and alkaline earth metal salts, such as salts of lithium, sodium, potassium, magnesium, and calcium. Examples of salts with organic bases include salts with primary, secondary, and tertiary aliphatic and aromatic amines (e.g., methylamine, ethylamine, propylamine, isopropylamine, 4 types of butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, benzathine, N-methyl-D-glucamine, 2-amino-2-(hydroxymethyl)-1,3-propanediol, hydrabamine); and salts with amino acids, such as arginine and lysine.

Compounds ($I_0$-A) to ($I_0$-E) of the present invention or salts thereof may also be provided as solvates. Examples of the solvates include hydrates and alcohol (e.g., methanol and ethanol) solvates.

The structural formula and physicochemical properties of Compound ($I_0$-A) (Compound (I-1)) are as shown below:

(1) Color of the substance: red
(2) Molecular weight: 706
(3) Molecular formula: $C_{37}H_{38}O_{14}$
(4) Mass analysis: ESI-MS (negative mode) Actual measurement: 705.2
(5) Ultraviolet absorption spectrum (in acetonitrile) λmax 217, 317, 424 nm
(6) $^1$H NMR (measured in deuterochloroform, 600 MHz) δppm 12.30 (s, 1H), 7.88 (d, J=8.3 Hz, 1H), 7.61 (d, J=7.6 Hz, 1H), 6.90 (d, J=9.6 Hz, 1H), 6.84 (dd, J=3.4, 10.3 Hz, 1H), 6.67 (dd, J=3.4, 10.3 Hz, 1H), 6.40 (d, J=9.6 Hz, 1H), 6.14 (d, J=10.3 Hz, 1H), 6.06 (d, J=9.6 Hz, 1H), 5.57 (d, J=3.4 Hz, 1H), 5.37 (d, J=3.4 Hz, 1H), 4.87 (d, J=11.0 Hz, 1H), 4.75 (q, J=6.2 Hz, 1H), 4.72 (d, J=6.8 Hz, 1H), 4.67 (brs, 1H), 4.28 (brs, 1H), 3.90 (m, 1H), 3.62 (s, 1H), 3.56 (m, 1H), 3.23 (m, 1H), 3.20 (m, 1H), 2.55 (m, 1H), 2.54 (m, 1H), 2.45 (dd, J=2.6, 15.8 Hz, 1H), 1.81 (d, J=15.8 Hz, 1H), 1.47 (s, 3H), 1.44 (d, J=3.4 Hz, 3H), 1.43 (d, J=4.1 Hz, 3H), 1.39 (d, J=6.2 Hz, 3H), 1.36 (m, 1H)
(7) $^{13}$C NMR (measured in deuterochloroform, 125 MHz) δppm 204.2, 196.8, 195.3, 188.1, 182.2, 158.1, 145.3, 142.8, 142.2, 138.8; 138.5, 138.4, 133.7, 130.5, 127.8, 127.4, 119.8, 117.4, 114.0, 95.2, 89.4, 88.8, 82.8, 79.4, 77.0, 74.4, 71.6, 71.3, 71.1, 70.7, 50.2, 42.7, 38.9, 26.5, 18.4, 15.2, 15.1
(8) Solubility: Soluble in methanol, dimethyl sulfoxide (DMSO), and chloroform. Slightly soluble in water.

The structural formula and physicochemical properties of Compound ($I_0$-B) are as shown below:

(1) Color of the substance: red
(2) Molecular weight: 708
(3) Molecular formula: $C_{37}H_{40}O_{14}$
(4) Mass analysis: ESI-MS (negative mode) Actual measurement: 707.2
(5) Ultraviolet absorption spectrum (in acetonitrile) λmax 218, 315, 423 nm
(6) $^1$H NMR (measured in deuterochloroform, 600 MHz) δppm 12.28 (brs, 1H), 7.88 (d, J=7.6 Hz, 1H), 7.61 (d, J=7.6 Hz, 1H), 6.89 (d, J=9.6 Hz, 1H), 6.42 (d, J=9.6 Hz, 1H), 5.40 (t, J=6.2 Hz, 1H), 5.17 (d, J=3.4 Hz, 1H), 4.95 (dd, J=1.4, 11.3 Hz, 1H), 4.71 (q, J=6.8 Hz, 1H), 4.58 (brs, 1H), 4.51 (q, J=6.9 Hz, 1H), 4.33 (m, 1H), 3.96 (brs, 1H), 3.80 (m, 1H), 3.56 (m, 1H), 3.48 (t, J=4.1 Hz, 1H), 3.28 (dd, J=3.4, 13.1 Hz, 1H), 2.62-2.66 (m, 2H), 2.51 (d, J=13.1 Hz, 1H), 2.43 (ddd, J=2.1, 4.8, 13.1 Hz, 1H), 2.38-2.40 (m, 2H), 2.35 (dd, J=3.4, 15.4 Hz, 1H), 2.30 (m, 1H), 2.16 (d, J=3.4 Hz, 1H), 1.79 (d, J=15.1 Hz, 1H), 1.45 (s, 3H), 1.40 (m, 1H), 1.39 (d, J=6.2 Hz, 3H), 1.38 (d, J=6.8 Hz, 3H), 1.37 (d, J=6.9 Hz, 3H)
(7) $^{13}$C NMR (measured in deuterochloroform, 125 MHz) δppm 211.0, 208.0, 204.5, 188.2, 182.3, 158.5, 145.3, 139.3, 139.1, 138.5, 133.7, 130.6, 119.8, 117.4, 114.6, 92.8, 91.4, 82.5, 79.9, 77.8, 77.4, 77.1, 74.6, 74.5, 71.5, 71.2, 71.0, 50.5, 44.1, 40.0, 36.7, 33.4, 28.3, 25.8, 17.5, 16.9, 14.8
(8) Solubility: Soluble in methanol, dimethyl sulfoxide (DMSO), and chloroform. Slightly soluble in water.

The structural formula and physicochemical properties of Compound ($I_0$-C) are as shown below:
(1) Color of the substance: red
(2) Molecular weight: 706
(3) Molecular formula: $C_{37}H_{38}O_{14}$
(4) Mass analysis: ESI-MS (negative mode) Actual measurement: 705.2
(5) Ultraviolet absorption spectrum (in acetonitrile) λmax 218, 316, 425 nm
(6) $^1$H NMR (measured in deuterochloroform, 600 MHz) δppm 12.20 (brs, 1H), 7.88 (d, J=7.6 Hz, 1H), 7.60 (d, J=7.6 Hz, 1H), 6.89 (d, J=9.6 Hz, 1H), 6.67 (dd, J=3.4, 10.3 Hz, 1H), 6.40 (d, J=9.6 Hz, 1H), 6.05 (d, J=10.3 Hz, 1H), 5.57 (d, J=3.4 Hz, 1H), 5.17 (d, J=2.8 Hz, 1H), 4.94 (dd, J=2.1, 11.0 Hz, 1H), 4.74 (q, J=7.6 Hz, 1H), 4.70 (q, J=7.6 Hz, 1H), 4.55 (brs, 1H), 4.32 (m, 1H), 3.81 (m, 1H), 3.56 (brs, 1H), 3.55 (m, 1H), 3.47 (m, 1H), 3.21 (dd, J=3.4, 13.8 Hz, 1H), 2.62-2.64 (m, 2H), 2.54 (d, J=13.8 Hz, 1H), 2.45 (m, 1H), 2.45 (dd, J=2.8, 15.8 Hz, 1H), 1.80 (d, J=15.8 Hz, 1H), 1.46 (s, 3H), 1.42 (d, J=6.9 Hz, 3H), 1.38 (m, 1H), 1.38 (d, J=6.2 Hz, 3H), 1.36 (d, J=7.6 Hz, 3H)
(7) $^{13}$C NMR (measured in deuterochloroform, 125 MHz) δppm 208.4, 208.4, 197.4, 188.8, 182.8, 158.5, 146.0, 143.4, 139.3, 139.1, 138.5, 134.3, 131.1, 128.3, 120.4, 117.9, 114.6, 92.0, 89.3, 83.3, 79.9, 78.4, 77.1, 75.2, 75.1, 72.1, 71.8, 71.3, 69.9, 50.8, 43.2, 40.6, 37.3, 27.1, 18.1, 16.8, 15.7
(8) Solubility: Soluble in methanol, dimethyl sulfoxide (DMSO), and chloroform. Slightly soluble in water.

The structural formula and physicochemical properties of Compound ($I_0$-D) are as shown below:
(1) Color of the substance: red
(2) Molecular weight: 822
(3) Molecular formula: $C_{43}H_{50}O_{16}$
(4) Mass analysis: ESI-MS (negative mode) Actual measurement: 821.3
(5) Ultraviolet absorption spectrum (in acetonitrile) λmax 219, 316, 429 nm
(6) $^1$H NMR (measured in deuterochloroform, 600 MHz) δppm 12.30 (brs, 1H), 7.87 (d, J=7.6 Hz, 1H), 7.60 (d, J=7.6 Hz, 1H), 6.90 (d, J=9.6 Hz, 1H), 6.87 (dd, J=3.6, 10.1 Hz, 1H), 6.41 (d, J=9.6 Hz, 1H), 6.04 (d, J=10.1 Hz, 1H), 5.40 (t, J=6.3 Hz, 1H), 5.25 (d, J=3.6 Hz, 1H), 4.97 (brs, 1H), 4.97 (brs, 1H), 4.86 (dd, J=1.4, 11.3 Hz, 1H), 4.58 (brs, 1H), 4.55 (q, J=6.7 Hz, 1H), 4.51 (q, J=6.6 Hz, 1H), 4.22 (m, 1H), 3.95 (brs, 1H), 3.79 (m, 1H), 3.70 (brs, 1H), 3.54 (m, 1H), 3.20 (dd, J=3.0, 13.1 Hz, 1H), 3.04 (t, J=8.4 Hz, 1H), 2.51 (d, J=13.1 Hz, 1H), 2.50 (m, 1H), 2.36-2.38 (m, 2H), 2.35 (dd, J=3.0, 15.2 Hz, 1H), 2.29 (m, 1H), 2.09 (m, 1H), 2.08 (m, 1H), 1.96 (m, 1H), 1.86 (m, 1H), 1.79 (d, J=15.2 Hz, 1H), 1.67 (m, 1H), 1.44 (s, 3H), 1.39 (d, J=6.6 Hz, 3H), 1.38 (d, J=6.7 Hz, 3H), 1.36 (m, 1H), 1.34 (d, J=6.0 Hz, 3H), 1.26 (d, J=6.8 Hz, 3H)
(7) $^{13}$C NMR (measured in deuterochloroform, 125 MHz) δppm 210.9, 204.5, 197.0, 188.2, 182.2, 158.1, 145.3, 142.8, 138.2, 138.1, 138.0, 133.7, 130.4, 127.5, 119.1, 117.4, 113.9, 98.9, 95.8, 92.8, 88.4, 82.5, 79.8, 76.7, 75.6, 73.9, 72.0, 70.8, 70.5, 70.2, 67.3, 50.5, 44.1, 38.2, 33.4, 28.3, 25.8, 24.6, 23.8, 18.5, 16.5, 14.8, 14.6
(8) Solubility: Soluble in methanol, dimethyl sulfoxide (DMSO), and chloroform. Slightly soluble in water.

The structural formula and physicochemical properties of Compound ($I_0$-E) (Compound (I-2)) are as shown below:
(1) Color of the substance: red
(2) Molecular weight: 820
(3) Molecular formula: $C_{43}H_{48}O_{16}$
(4) Mass analysis: ESI-MS (negative mode) Actual measurement: 819.4
(5) Ultraviolet absorption spectrum (in acetonitrile) λmax: 218, 317, 428 nm
(6) Specific rotation $[\alpha]_D$ +84 (c=0.2, methanol, 25° C.) The specific rotation $[\alpha]_D$ of the hydrolysate aglycone of Compound (I-2) was +119 (c=0.07, methanol, 25° C.).
(7) $^1$H NMR (measured in deuterochloroform, 600 MHz) δppm 12.30 (s, 1H), 7.86 (d, J=7.5 Hz, 1H), 7.59 (d, J=7.5 Hz, 1H), 6.86 (dd, J=3.4, 10.3 Hz, 1H), 6.67 (dd, J=4.1, 10.3 Hz, 1H), 6.39 (d, J=9.6 Hz, 1H), 6.09 (d, J=10.3 Hz, 1H), 6.04 (d, J=10.3 Hz, 1H), 5.57 (d, J=4.1 Hz, 1H), 5.24 (d, J=3.4 Hz, 1H), 4.97 (brs, 1H), 4.93 (brs, 1H) 4.83 (dd, J=1.4, 10.3 Hz, 1H), 4.71 (q, J=6.2 Hz, 1H), 4.57 (s, 1H), 4.55 (d, J=6.9 Hz, 1H), 4.22 (dq, J=1.5, 6.8 Hz, 1H), 3.79 (m, 1H), 3.69 (brs, 1H), 3.54 (m, 1H), 3.20 (dd, J=3.4, 13.0 Hz, 1H), 3.04 (m, 1H), 2.53 (d, J=13.0 Hz, 1H), 2.49 (ddd, J=1.4, 5.2, 13.1 Hz, 1H), 2.44 (dd, J=3.4, 15.1 Hz, 1H), 2.10 (m, 1H), 2.08 (m, 1H), 1.93 (m, 1H), 1.80 (d, J=15.1 Hz, 1H), 1.68 (m, 1H), 1.45 (s, 3H), 1.41 (d, J=6.9 Hz, 3H), 1.37 (d, J=6.2 Hz, 3H), 1.36 (dd, J=5.2, 13.1 Hz, 1H), 1.34 (d, J=6.2 Hz, 3H), 1.25 (d, J=6.8 Hz, 3H)
(8) $^{13}$C NMR (measured in deuterochloroform, 125 MHz) δppm 203.6, 196.3, 196.1, 187.6, 181.8, 157.6, 144.8, 142.4, 142.2, 138.2, 138.1, 138.0, 133.2, 129.9, 127.1, 127.0, 119.3, 116.8, 113.4, 98.9, 94.8, 88.4, 88.2, 82.3, 78.8, 76.7, 75.6, 74.0, 70.9, 70.5, 70.2, 70.1, 67.3, 49.7, 42.1, 38.2, 26.0, 24.6, 23.8, 18.0, 16.5, 14.7, 14.6
(9) Solubility: Soluble in methanol, dimethyl sulfoxide (DMSO), and chloroform. Slightly soluble in water.

2. Production of the Compound of the Invention 2.1. Production of the Compound Represented by Formula ($I_0$)

The compound represented by Formula ($I_0$) of the invention can be produced by culturing microorganisms in a medium to produce and accumulate the compound in a culture product, and collecting the compound from the culture product.

(1) Microorganisms

Microorganisms usable in the production method of the invention are not limited, as long as they belong to the genus *Streptomyces* and are capable of producing the compound represented by Formula ($I_0$) above. Examples of such microorganisms include *Streptomyces* sp. TK08046, variants from this strain, and similar strains of this strain. *Streptomyces* sp. TK08046 was received on Aug. 30, 2011 at the NITE Patent Microorganisms Depositary (NPMD, 2-5-8 Kazusakamatari, Kisarazu-city, Chiba, Japan) under reference number NITE AP-1138, and domestically deposited under accession number NITE P-1138. The *Streptomyces* sp. TK08046 was then transferred to international deposition under the Budapest Treaty on Oct. 2, 2012 (accession number NITE BP-1138). This strain is capable of producing the compound of ($I_0$) above.

The "variants" used herein are those obtained through mutation-inducing treatment using arbitrary mutagens. The term "mutagen" should be interpreted to include the meaning of, in its broad sense, for example, not only drugs having mutagenic effects, but also treatments that provide mutagenic effects, such as UV irradiation. Examples of appropriate mutagens include ethyl methanesulfonate, UV irradiation, N-methyl-N'-nitro-N-nitrosoguanidine, bromouracil, and like nucleotide base analogs; and acridines. It is also possible to use any other effective mutagens.

Examples of "similar strains" as used herein include a strain harboring 16S rDNA gene having a base sequence with homology of 95% or more to the base sequence of 16S rDNA gene of *Streptomyces* sp. TK08046 (shown as SEQ ID NO: 1). It is sufficient if the homology of 16S rDNA gene is 95% or more; however, the homology is preferably 97% or more, more preferably 98% or more, and most preferably 100%.

PCR was performed to determine the 16S rDNA base sequences of *Streptomyces* sp. TK08046 using primers, 10F, 686F, 800R, and 1541R, that can amplify almost full-length eubacterial 16S rDNA. As a result of a BLAST search using the determined 1516 base sequences, the top 30 of those having high homology were *Streptomyces* sp. or actinomycetes belonging to an unclassified genus; all of these had homology of 98% or more. This strain was thus classified into *Streptomyces* sp.

The bacteriological properties of *Streptomyces* sp. TK08046 are as follows:
1) Cell shape: mycelial form;
2) Presence or absence of spores: presence;
3) Starch casein medium: grows in an excellent manner, and the colony is circular, has a pedestal shape, a mycelial form, and is completely brown;
4) Starch casein liquid medium: grows in an excellent manner;
5) Starch hydrolysis: yes;
6) Dye formation: dark brown dyes formed in agar medium and liquid medium; and
7) Growth range (pH): pH of 6 to 9.

(2) Culture of Microorganisms

Culture of microorganisms is performed in this invention according to a known method for culturing microorganisms. Any synthetic medium or natural medium may be used, as long as the medium arbitrarily contains assimilable carbon and nitrogen sources, inorganic substance, and required growth-/production-promoting substances. Examples of carbon sources include glucose, starch, dextrin, mannose, fructose, sucrose, lactose, xylose, arabinose, mannitol, molasses, and the like. These may be used singly, or in a combination of two or more. Additionally, hydrocarbons, alcohols, organic acids, amino acids (e.g., tryptophan), and the like, may also be used, if necessary. Examples of nitrogen sources include ammonium chloride, ammonium sulfate, ammonium nitrate, sodium nitrate, urea, peptone, meat extract, yeast extract, dry yeast, corn steep liquor, soybean flour, cottonseed meal, casamino acid, and the like. These may be used singly, or in a combination of two or more. Additionally, sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, and like inorganic salts may be added, if necessary. Further, a minor component that promotes the growth of microorganisms used or the production of the compound of the invention may be appropriately added. A person skilled in the art can appropriately select such a component.

As a culture method, liquid culture is suitable, although it is not limited thereto. An appropriate culture temperature is in the range of 25 to 37° C. It is desirable to maintain the pH of the medium during culture at 7 to 9. A rotary or reciprocal shaking culture is desirably performed at a shaking rate of 30 to 120 rpm. In general, when liquid culture is performed for 5 to 14 days, a target compound is produced and accumulated in the culture liquid and bacterial cells. The culture is terminated when the production amount in the culture product reached a maximum.

(3) Isolation and Purification of Compound

Isolation and purification of the compound of the invention from the culture product is conducted by a method generally employed to isolate and purify a microbial metabolite from its culture product. The "culture product" used herein indicates any of culture supernatant, culture bacterial cells, and disruptions of bacterial cells. For example, a culture product is separated into a culture filtrate and bacterial cells by filtration and centrifugation. The filtrate is extracted with ethyl acetate or other organic solvents. Further, the culture filtrate is extracted with ethyl acetate, chloroform, or the like. Subsequently, the extract is concentrated and subjected to purification using column chromatography, preparative thin-layer chromatography, high-performance liquid chromatography, or the like, to obtain the compound of the invention. The obtained compound is analyzed for whether it has the properties described in "1. The properties of the compound of the present invention" above by NMR analysis or other general chemical methods. In this manner, it is possible to confirm that the obtained compound is the compound of the invention.

The kinetics of the compound of the invention during culture and purification operation can be traced by means of a high-performance liquid chromatography with photodiode array detector, using the ultraviolet absorption as an index.

3. Use of the Compound of the Present Invention

The compound of the present invention exhibits potent growth inhibitory activity on fungi, particularly oomycetes, as shown in the following Examples; therefore, the compound of the invention can be used as an antifungal agent. Antifungal agents comprising the compound of the present invention as an active ingredient can be used as prophylactic or therapeutic agents for, for example, fish fungal diseases such as saprolegniasis in eel; saprolegniasis in coho salmon, rainbow trout, etc.; visceral mycosis in salmoid fry; saprolegniasis in pejerrey (*Odontesthes bonariensis*); mycotic granulomatosis in ayu (*Plecoglossus altivelis*); and preferably as anti-saprolegniasis drugs for fish (saprolegniasis prophylactic or therapeutic agents). Further, the compound of the present invention is effective as an agent for controlling plant diseases caused by oomycetes.

To use the compound of the present invention as a prophylactic or therapeutic agent for fish fungal diseases, the compound of the invention may, for example, be mixed into fish feed; added to a culture tank; or mixed with the gravel of a culture tank. Alternatively, other methods can also be used: fish or fish eggs may be immersed in water or sea water containing about 0.001 to 0.1 wt. % of the compound of the invention; a suspension containing about 0.001 to 0.1 wt. % of the compound of the invention may be sprayed over the entire bodies of the fish or the entire eggs; or fish may be intravenously or intraperitoneally inoculated using a syringe with a suspension containing about 0.001 to 0.1 wt. % of the compound of the invention.

EXAMPLES

The present invention is described in detail below with reference to Examples. However, the technical scope of the present invention is not limited by the Examples.

Production of Compound of Formula ($I_0$)

*Streptomyces* sp. TK08046 was used as a bacterium for producing the compound of Formula ($I_0$). The strain was cultured by rotary shaking (100 rpm) at 30° C. for 5 days in a 500-mL Erlenmeyer flask with baffles containing 200 mL of starch casein medium (starch: 1.0%, casein: 0.03%, NaCl: 0.2%, $K_2HPO_4$: 0.2%, $MgSO_4$: 0.005%, $CaCO_3$: 0.002%, $FeSO_4 \cdot 7H_2O$: 0.001% (W/V), pH: 7.2) to obtain an inoculum for subsequent mass cultivation. The inoculum culture product was inoculated in three 2-L Sakaguchi flasks each containing 600 mL of starch casein medium (1.8 L in total), in an amount of 10 mL per flask, and cultured by reciprocal shaking (110 rpm) at 30° C. for 7 days. During culture, the pH of the medium was not controlled.

The thus-obtained culture medium (1.8 L) was filtered and separated into the bacterial cells and the filtrate. The filtrate was extracted 3 times with an equivalent amount of ethyl acetate. The obtained extract was purified by ODS silica gel column chromatography. Wakogel 50C18 (Wako Pure Chemical Industries, Ltd.) was used as a carrier. Acetonitrile water with concentrations of 10%, 30%, 50%, and 70%, and 100% acetonitrile were used as mobile phases in this order. Anti-oomycete activity was observed in the fractions eluted with acetonitrile water with concentrations of 30 to 70% and 100% acetonitrile.

Next, these fractions were purified by high-performance liquid chromatography (column: Cosmosil 5C18ARII (diameter: 10 mm, length: 250 mm); mobile phase: 60% acetonitrile water; flow rate: 3 mL/min, detection wavelength: 220 nm). As a result of the culture, and from the culture product, 3.1 mg of Compound (I-1) of the present invention, 1.1 mg of Compound ($I_0$-B), 1.9 mg of Compound ($I_0$-C), 2.7 mg of Compound ($I_0$-D), and 8.1 mg of Compound (I-2) were obtained from a total of 1.8 L of the culture product.

Compounds (I-1), ($I_0$-B), ($I_0$-C), ($I_0$-D), and (I-2) were measured for activity against various microorganisms. Compounds (I-1) and (I-2) were further measured for activity against phytoplankton (green algae) and zooplankton (water flea). The activity of "Pyceze" (trade name, produced by Novartis Animal Health K.K.), a commercially available saprolegniasis prophylactic agent, was also measured for comparison.

Measurement of Antimicrobial Activity

The activity against eukaryotic microorganisms was measured with a 96-well microplate in the following manner. Compound (I-1), ($I_0$-B), ($I_0$-C), ($I_0$-D), or (I-2) was suspended in 8% methanol water to prepare a sample suspension having a concentration of 4000, 2000, 1000, 500, 250, 125, 62.5, 32, 16, 8, or 4 µg/mL. Pyceze was diluted with water to prepare Pyceze aqueous solutions having the above concentrations. 50 µl of each of the sample solutions having the above concentrations, 50 µl of sterilized 4-fold concentrated liquid medium, and 100 µl of spore suspension or bacterial suspension of the test organisms prepared beforehand were poured in each well of the 96-well microplate. The experiments were performed in duplicate. After culture was performed for a certain period of time at a temperature depending on each test organism, the growth of the microorganism was observed with an inverted microscope to determine the presence of activity. The test organisms and the culture conditions were as follows.

*Saprolegnia parasitica*: GY medium (glucose: 1%, yeast extract: 0.25%, pH: 6.5), 18° C., 24 hours;

*Phoma* sp.: YPD medium (yeast extract: 1%, peptone: 2%, glucose: 2%, pH: 6.5), 30° C., 30 hours; and

*Saccharomyces cerevisiae*: Sabouraud medium (maltose: 4%, peptone: 1%, pH: 6.0), 30° C., 30 hours.

The activity against prokaryotic microorganisms was measured by the paper disc method on an agar plate medium into which test organisms were kneaded. *Staphylococcus aureus*, *Bacillus subtilis*, or *Escherichia coli* was inoculated in 3 mL of sterilized LB medium (glucose: 0.5%, polypeptone: 1%, yeast extract: 0.5%, NaCl: 0.5%, pH: 7.2) in a test tube, and cultured at 37° C. overnight. The pre-culture solution (1%) was inoculated in a sterilized LB agar medium (agar: 1.5%) to prepare an agar assay plate. Compound (I-1) or (I-2) was dissolved in methanol to prepare a sample solution having a concentration of 1000, 500, 250, 125, 62.5, 32, 16, 8, 4, 2, or 1 µg/mL. The sample solution was infiltrated into a paper disc (ADVANTEC, diameter: 8 mm, thick), followed by air-drying. The paper disc was placed on the agar assay plate, and cultured at 37° C. overnight. The formation of inhibition rings around the paper disc was observed to determine the presence of activity.

Activity Test Against Algae

150 µL of algal culture solution in the logarithmic growth phase, and 50 µL of a sample solution suspended in 8% methanol water having a concentration of 400, 200, 100, 50, 25, 12.5, or 6.25 µg/mL, or a Pyceze aqueous solution having the above concentrations were added to each well of a 96-microwell plate. After incubation, cell proliferation was examined with an inverted microscope. Then, when the cell proliferation was found to be substantially the same as that of the positive control, the presence of activity was determined. *Chlorella vulgaris* (green algae) was cultured in a C medium to obtain a culture solution having $0.987 \pm 0.470 \times 10^7$ cells/mL, and incubated under a condition of 25° C., 30 µmol, and photons/$m^2$/s. As a positive control, cycloheximide (final concentration=100 µg/mL) was also incubated under the same condition.

Water Flea (*Daphnia Pulex*) Swimming Ability Inhibitory Activity Test

The number of water fleas was adjusted so that each 10 mL of aerated water contained 5 fleas. The water fleas were all 24 hours old after birth or younger. The aerated water was prepared by aerating tap water, which had been filtered by a water cleaner, for at least 24 hours. A sample solution obtained by dissolving Compound (I-1) or (I-2) in methanol, or a Pyceze aqueous solution obtained by diluting Pyceze with water, was added to the water flea breeding water under stirring so that the final concentration of the sample or Pyceze became 100, 10, 1, 0.1, or 0.01 µg/mL. After incubation for 24 hours (20° C., 17 µmol photons/$m^2$/s, Light:Dark=16:8), the number of water fleas swimming in the breeding water was counted. The water fleas were divided into multiple groups, each consisting of 5 fleas. Using 2 groups each, an experiment was performed with the test liquids having the aforementioned different final concentrations. From the obtained results, $IC_{50}$ values were calculated according to the probit method using SPSS statistical software.

The minimum inhibitory concentration (MIC) with respect to eukaryotic microorganisms was found as follows. The minimum inhibitory concentration (MIC) of Compound (I-1), Compound ($I_0$-B), Compound ($I_0$-C), Compound ($I_0$-D), and Compound (I-2) with respect to *Saprolegnia parasitica* was 0.0039 µg/mL, 8 µg/mL, 1 µg/mL, 1 µg/mL, and 0.0078 µg/mL, respectively. In contrast, the MIC of Pyceze, which was used for comparison, with respect to *Saprolegnia parasitica* was 5.0 µg/mL. None of Compounds (I-1), ($I_0$-B), ($I_0$-C), ($I_0$-D), and (I-2), even in an amount of 1000 µg/mL, had a growth inhibition effect against *Saccharomyces cerevisiae*. The MIC with respect to *Phoma* sp. was 500 µg/mL for all of Compounds (I-1), ($I_0$-B), ($I_0$-C), ($I_0$-D) and (I-2).

The minimum inhibitory concentration (MIC) with respect to prokaryotic microorganisms was found as follows. The minimum inhibitory concentration of Compound (I-1), Compound ($I_0$-B), Compound ($I_0$-C), Compound ($I_0$-D), and Compound (I-2) with respect to *Staphylococcus aureus* were 31.2 µg/mL, 250 µg/mL, 125 µg/mL, 62.5 µg/mL and 16.0 µg/mL, respectively, and an inhibition ring was observed on each agar medium. The minimum inhibitory concentrations of Compound (I-1), Compound ($I_0$-B), Compound ($I_0$-C), Compound ($I_0$-D), and Compound (I-2) with respect to *Bacillus subtilis* were 62.5 µg/mL, 250 µg/mL, 250 µg/mL, 62.5 µg/mL, and 8.0 µg/mL, respectively, and an inhibition ring was observed on each agar medium. However, for *Escherichia coli*, an inhibition ring was not observed in any samples using Compounds (I-1), ($I_0$-B), ($I_0$-C), ($I_0$-D), and (I-2).

Further, both of Compounds (I-1) and (I-2), even in an amount of 100 µg/mL, had no influence on green algae (*Chlorella vulgaris*), which is an organism in the aquatic environment; however, the MIC of Pyceze used for comparison with respect to green algae (*Chlorella vulgaris*) was 62.5 µg/mL. Further, the 50% swimming ability inhibitory concentrations of Compounds (I-1) and (I-2) with respect to water flea (*Daphnia pulex*), which is an arthropod, were 2.58 µg/mL and 4.48 µg/mL, respectively. The 50% swimming ability inhibitory concentration of Pyceze used for comparison with respect to water flea was 3.7 µg/mL.

The results revealed that Compounds (I-1), ($I_0$-B), ($I_0$-C), ($I_0$-D), and (I-2) have high activity against *Saprolegnia parasitica*, and thus exhibit an anti-saprolegnia effect even at a very low concentration; however, Compounds (I-1), ($I_0$-B), ($I_0$-C), ($I_0$-D), and (I-2) have low activity against other eukaryotic microorganisms and prokaryotic microorganisms. Accordingly, Compounds (I-1), ($I_0$-B), ($I_0$-C), ($I_0$-D), and (I-2) are assumed to have selective anti-saprolegnia activity. Further, Compounds (I-1) and (I-2) have a very low effect on environmental organisms (ecosystem).

[Accession Number]

NITE BP-1138

[Sequence Table]

The invention claimed is:

1. A compound represented by Formula ($I_0$) or a salt thereof:

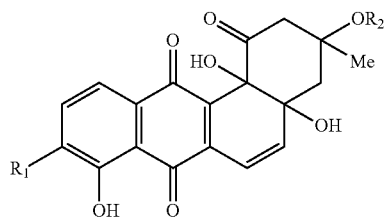

wherein $R_1$ is:

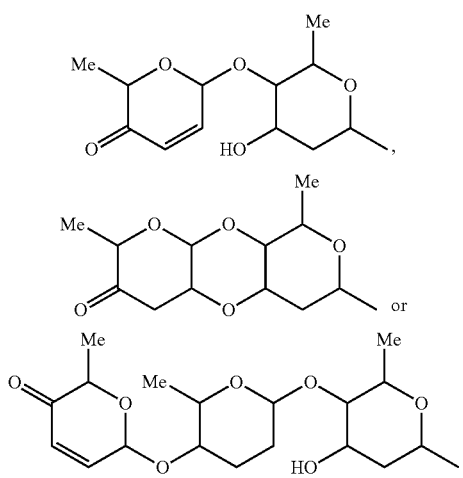

and $R_2$ is:

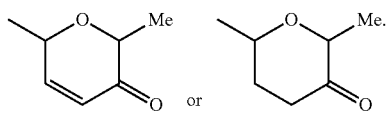

2. A compound represented by Formula (I) or a salt thereof:

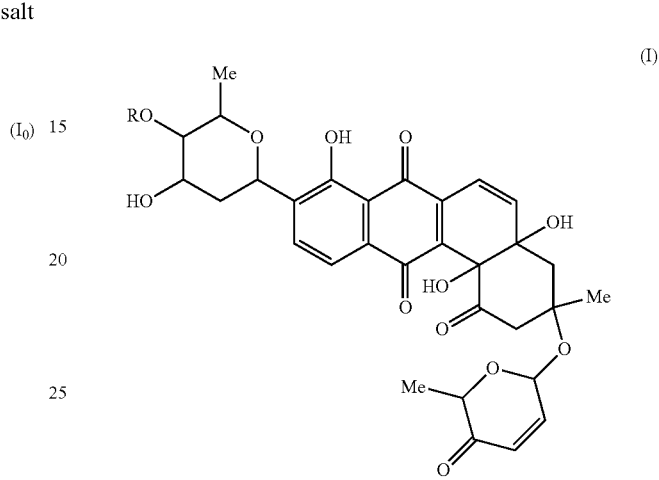

wherein R is:

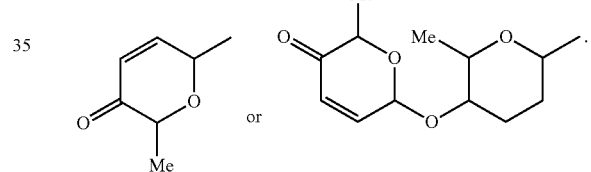

3. A method for producing the compound of claim 1,
the method comprising culturing a microorganism belonging to the genus *Streptomyces* having the ability to produce the compound of claim 1 in a medium to produce and accumulate the compound in a culture product; and collecting the compound.

4. An antifungal agent comprising the compound of claim 1 as an active ingredient.

5. A method for producing the compound of claim 2,
the method comprising culturing a microorganism belonging to the genus *Streptomyces* having the ability to produce the compound of claim 2 in a medium to produce and accumulate the compound in a culture product; and collecting the compound.

6. An antifungal agent comprising the compound of claim 2 as an active ingredient.

* * * * *